United States Patent [19]

Tikijian

[11] Patent Number: 5,357,781
[45] Date of Patent: Oct. 25, 1994

[54] METHOD AND APPARATUS FOR SAMPLING AND DETECTING GASES IN A FLUID

[75] Inventor: George H. Tikijian, Zionsville, Ind.

[73] Assignee: SenTech Corporation, Indianapolis, Ind.

[21] Appl. No.: 8,369

[22] Filed: Jan. 22, 1993

[51] Int. Cl.$^5$ .................... G01M 3/04; G01N 1/10
[52] U.S. Cl. .................. 73/19.1; 73/19.12; 340/632
[58] Field of Search ............. 340/632; 73/19.01, 19.1, 73/19.12

[56] References Cited

U.S. PATENT DOCUMENTS

| | | | |
|---|---|---|---|
| 1,906,526 | 5/1933 | Bradford | 55/178 |
| 2,379,133 | 6/1945 | Curtis | 103/113 |
| 2,463,251 | 3/1949 | Curtis | 103/113 |
| 2,987,912 | 6/1961 | Jacobson | 73/19.1 |
| 3,069,898 | 12/1962 | Vesper | 73/23.42 |
| 3,150,516 | 9/1964 | Linnenbom et al. | 73/19.1 |
| 3,298,227 | 1/1967 | Hicks | 73/863.33 |
| 3,369,405 | 2/1968 | Galegar | 73/421 |
| 3,699,802 | 10/1972 | Hotta et al. | 73/40.5 R |
| 3,827,302 | 8/1974 | Sato | 73/422 GC |
| 3,846,075 | 11/1974 | Cioffi | 73/863.33 |
| 4,090,392 | 5/1978 | Smith et al. | 73/421.5 R |
| 4,119,950 | 10/1978 | Redding | 340/632 |
| 4,154,086 | 5/1979 | Button et al. | 73/19 |
| 4,184,359 | 1/1980 | Gracey | 73/19 |
| 4,192,175 | 3/1980 | Godai et al. | 73/863.33 |
| 4,209,359 | 6/1980 | Sethy | 162/29 |
| 4,326,863 | 4/1982 | Day et al. | 55/171 |
| 4,414,858 | 11/1983 | Peterson et al. | 73/863.33 |
| 4,472,354 | 9/1984 | Passell et al. | 422/62 |
| 4,546,640 | 10/1985 | Stone et al. | 73/19.09 |
| 4,565,086 | 1/1986 | Orr, Jr. | 73/23 |
| 4,618,855 | 10/1986 | Harding et al. | 73/40 |
| 4,663,724 | 5/1987 | Onizuka et al. | 73/19.1 |
| 4,731,732 | 3/1988 | Warchol et al. | 364/510 |
| 4,763,514 | 8/1988 | Naito et al. | 73/19.01 |
| 4,764,344 | 8/1988 | Knab | 73/19.01 |
| 4,910,463 | 3/1990 | Williams, II et al. | 324/468 |
| 4,993,271 | 2/1991 | Vargason | 73/863.33 |
| 5,044,761 | 9/1991 | Yuhki et al. | 366/139 |
| 5,062,292 | 11/1991 | Kanba et al. | 73/19.01 |
| 5,115,666 | 5/1992 | Williams | 73/19.1 |

FOREIGN PATENT DOCUMENTS 8900482 2/1989 Netherlands .

Primary Examiner—Robert Raevis
Assistant Examiner—Michael Brock
Attorney, Agent, or Firm—Arter & Hadden

[57] ABSTRACT

There is disclosed a method and apparatus for repetitively taking samples of a predetermined quantity of a test gas in a liquid and introducing these samples to a test chamber. Each sample is agitated to release therefrom the test gas. The released gas is then conveyed to a sensor, which monitors the released gas for the presence of a concentration above the threshold level to produce an alarm indicative thereof. The samples of the test gas in a liquid may be repetitively taken from one zone of a plurality at a time until each zone is sampled. After one sample has been tested in the test chamber, it is discharged therefrom and the test chamber is flushed with a sample of the liquid and test gas taken from the next zone of the plurality before introducing the next sample from the same, next zone.

25 Claims, 7 Drawing Sheets

METHOD AND APPARATUS FOR SAMPLING AND DETECTING GASES IN A FLUID

FIELD OF THE INVENTION

The present invention relates to apparatus and methods of taking samples of gases and fluids and of continuously monitoring a sequence of such samples for the presence of a particular gas. The fluid may be either a gas or a liquid. Further, the method and apparatus of this invention are capable of taking samples from a plurality of zones or sources and, in particular, for sampling and monitoring gas/gas samples and liquid/gas samples.

CROSS-REFERENCE TO CO-PENDING APPLICATIONS

Reference is made to the following commonly assigned, copending applications:
1) U.S. Ser. No. 07/965,442, filed on Oct. 23, 1992 in the name of George H. Tikijian and entitled "Method And Apparatus For Monitoring For the Presence Of A Gas", which is incorporated herein by reference.
2) U.S. Ser. No. 07/886,231, filed May 21, 1992 in the name of William J. Williams, and entitled "Halogen Monitoring Apparatus", which is incorporated herein by reference.

BACKGROUND OF THE INVENTION

In industrial systems, and particularly, in refrigeration and air conditioning systems, the mixing of water with liquid refrigerants is undesirable. For example, the presence of excess water in liquid refrigerants may freeze at low temperatures and restrict or completely prevent the flow of expansion valves, capillary tubes, and the like.

In addition, the solubility of amounts of refrigerant in liquids such as water is of considerable concern in refrigeration systems such as drinking water coolers, water cooled condensers and the like where small amounts of the refrigerant are introduced with water or other liquids either through equipment failure, or in some instance, by faulty design. The presence of excess water in halogen may cause corrosion in the system. In particular, such water may cause the hydrolysis of leaky halogenated refrigerant with the formation of acids. These acids tend to corrode metals as well as insulation and other nonmetallic parts of the system. This condition is especially problematic during charging of the refrigeration system. Accordingly, detection of the halogen contaminant is essential to the operation and maintenance of these systems.

Refrigerant loss imposes an expense in at least two ways. First, the unit cost of a refrigerant is high and the total replacement cost of the lost refrigerant, particularly from large commercial refrigeration and air conditioning systems, can be very expensive. Secondly, if a refrigeration system fails due to refrigerant loss, there is the possible spoilage and loss of the refrigerated contents. It is desired to detect the existence of the refrigerant leak before the refrigerant loss has become great enough to degrade equipment performance. Further, leakage of refrigerants and in particular those comprising halogen may well degrade the environment.

In a typical refrigeration or air conditioning system, there are at least first and second loops. The first is a closed loop for circulating a refrigerant, typically a well known halogen refrigerant. The first, refrigerant loop includes a motor-driven compressor for compressing the inputted halogen, thus converting the halogen refrigerant from a gaseous to a liquid state and outputting a heated halogen liquid. The heated halogen is supplied to a condenser, which cools the halogen liquid. Typically, such condensers include a serpentine shaped tube, typically made of copper, for receiving and circulating the warm liquid halogen, and a shell for enclosing the serpentine shaped tube and circulating water thereabout, whereby the liquid halogen is cooled. The cooled liquid halogen is next directed through an expansion valve and into an evaporator. As the halogen changes from a gaseous to a liquid state, it absorbs heat thereby providing significant cooling. The cooled halogen gas is returned through the first loop from the evaporator to the compressor, whereby this cycle continues.

A trouble point in such refrigeration systems occurs in the condenser when the water circulating over the copper tubing wears by friction between the water and the tubing, holes in the tubing, thereby causing a mixing of the halogen and water. Most (but not all) refrigerants are circulated in the first, refrigeration loop under positive pressure so that when a leak occurs in the condenser tubing, halogen will flow into the cooling water and mix in the water therein. The second loop in which the cooling water flows varies from refrigeration system to refrigeration system. In some systems, the cooling water may be drawn from a river and after cooling returned to the river. In other refrigeration systems 10 such as shown in FIG. 1, the cooling water may be passed from a condenser 12 via a circulating conduit 16a to a cooling tower 14 and allowed to fall down over a series of baffles. Typically, such water towers are open to the atmosphere, whereby if there has been a halogen leak, the flow of water and halogen is exposed to the atmosphere with possible damage to the environment and in particular to the ozone layer. As shown in FIG. 1, the flow is returned from the cooling tower 14 to the condenser 12.

In those refrigeration or air conditioning systems where the refrigerant is maintained under a negative pressure, water will be drawn through the holes into the first refrigerant loop. Thereafter, the flow of water and halogen is returned from the evaporator to the condenser. Significant cooling of that flow takes place in the evaporator, whereby the water is converted to ice. When that ice is introduced into the compressor, the ice may readily damage the compressor and its motor, thereby bringing the operation of that refrigeration system to a halt.

Alternatively, there are refrigeration or air conditioning systems which incorporate an evaporator acting as a heat exchange device, whereby the expanding halogen gas passes through the evaporator in the form of a serpentine shaped coil surrounded by a shell for receiving a liquid, typically water, to be cooled. The water circulating over the evaporator tube may cause holes to wear therein, whereby a mixing of the halogen and water occurs. In such an embodiment, the cooled water is typically circulated through a second closed loop to cool an environment and thereafter return to be recooled by the evaporator. As described above, the presence of water and halogen is particularly corrosive. In those instances where the refrigerant is positively pressurized, halogen will be forced through the tube holes into the second closed cooling loop, thus contaminating the circulated water. Eventually, there is a strong possibility that the second loop will be corroded to the extent that holes will develop therein, whereby the water contaminated with halogen will leak directly into the surrounding environment. Again, possible contamination of the environment is likely.

In either of the above described refrigeration systems, wearing and contamination may occur with the result that water may become contaminated with the halogen. Therefore, it is important to be able to detect the presence of halogen mixed with water so that contaminated refrigeration systems may be shut down as early as possible and detected leaks of halogen repaired.

In U.S. Pat. No. 5,115,666, which is assigned to the assignee of this invention, there is disclosed a method of detecting halogen in a sample of halogen and a liquid by introducing that sample into a test chamber and heating that sample to a temperature dependant upon the solubility of the liquid in halogen to provide a vapor solution of halogen and liquid. The sample is subjected to an evaporation temperature selected to minimize the liquid portion of the vapor solution. The vapor solution is conveyed to a gas detector, which operates to detect a concentration of the halogen gas above a threshold level. Illustratively, that detector may comprise the detector described in U.S. Pat. No. 4,910,463, which is assigned to the assignee of this invention and which is incorporated herein by reference.

Heating samples of a halogen gas and a liquid has proven by continued observation to release a relative small percentage of the halogen gas disposed into the liquid. Further, it has been observed that calibrated samples of water with a known quantity of a test gas, e.g., a refrigerant has not yielded consistent measurement results by the use of the detector described in U.S. Pat. No. 4,910,463. Further, the introduction of consecutive cycles into the test chamber described in U.S. Pat. No. 5,115,666 without a cleansing of that test chamber, would lead to the contamination of the second sample and possible false gas concentration readings of the sample taken from a second source or zone.

SUMMARY OF THE INVENTION

It is therefore a general object of the present invention to provide an improved method and apparatus for taking samples of a test gas in a liquid taken from a corresponding plurality of zones or sources, and monitoring the samples for the presence of the test gas having a concentration above a threshold level.

It is an additional object of the present invention to more accurately detect the presence of the test gas in a liquid and, more particularly, for efficiently releasing the test gas from its liquid.

It is a still further object of this invention to efficiently take samples of both a test gas in a liquid and in another or ambient gas, and for monitoring these samples to detect the presence of the test gas of a concentration above the threshold level.

Other objects and advantages of the invention will become apparent upon reading the following description and appended claims, and upon reference to the accompanying drawings.

These and other objects of this invention are achieved with a method and apparatus for repetitively taking samples of a predetermined quantity of a test gas in a liquid and introducing these samples to a test chamber. Each sample is agitated to release therefrom the test gas. The released gas is then conveyed to a sensor, which monitors the released gas for the presence of a concentration above the threshold level to produce an alarm indicative thereof.

In a further aspect of this invention, the samples of the test gas in a liquid may be repetitively taken from one zone of a plurality at a time until each zone is sampled. After one sample has been tested in the test chamber, it is discharged therefrom and the test chamber is flushed with a sample of the liquid and test gas taken from the next zone of the plurality before introducing the next sample from the same, next zone.

In a still further aspect of this invention, the monitoring apparatus repetitively takes first samples of the test gas and a liquid from a plurality of corresponding first spaces and also takes second samples of the test gas and another gas from a plurality of corresponding second spaces. Only one sample from the first and second spaces is applied to the gas detection means at a time.

BRIEF DESCRIPTION OF THE DRAWINGS

For a more complete understanding of this invention, reference should now be made to the embodiment illustrated in greater detail in accompanying drawings and described below by way of example of the invention.

DETAILED DESCRIPTION OF THE PREFERRED EMBODIMENT

The following detailed description will permit a more complete understanding of this invention. However, the embodiment described below is simply an example of the invention, and the invention will not be limited to this embodiment. It will be understood that the methods and apparatus of the invention may be implemented with the use of various configurations with appropriate modification. It will be further understood, that in certain instances, details may have been omitted which are not necessary for an understanding of the present invention.

Figure 2A:
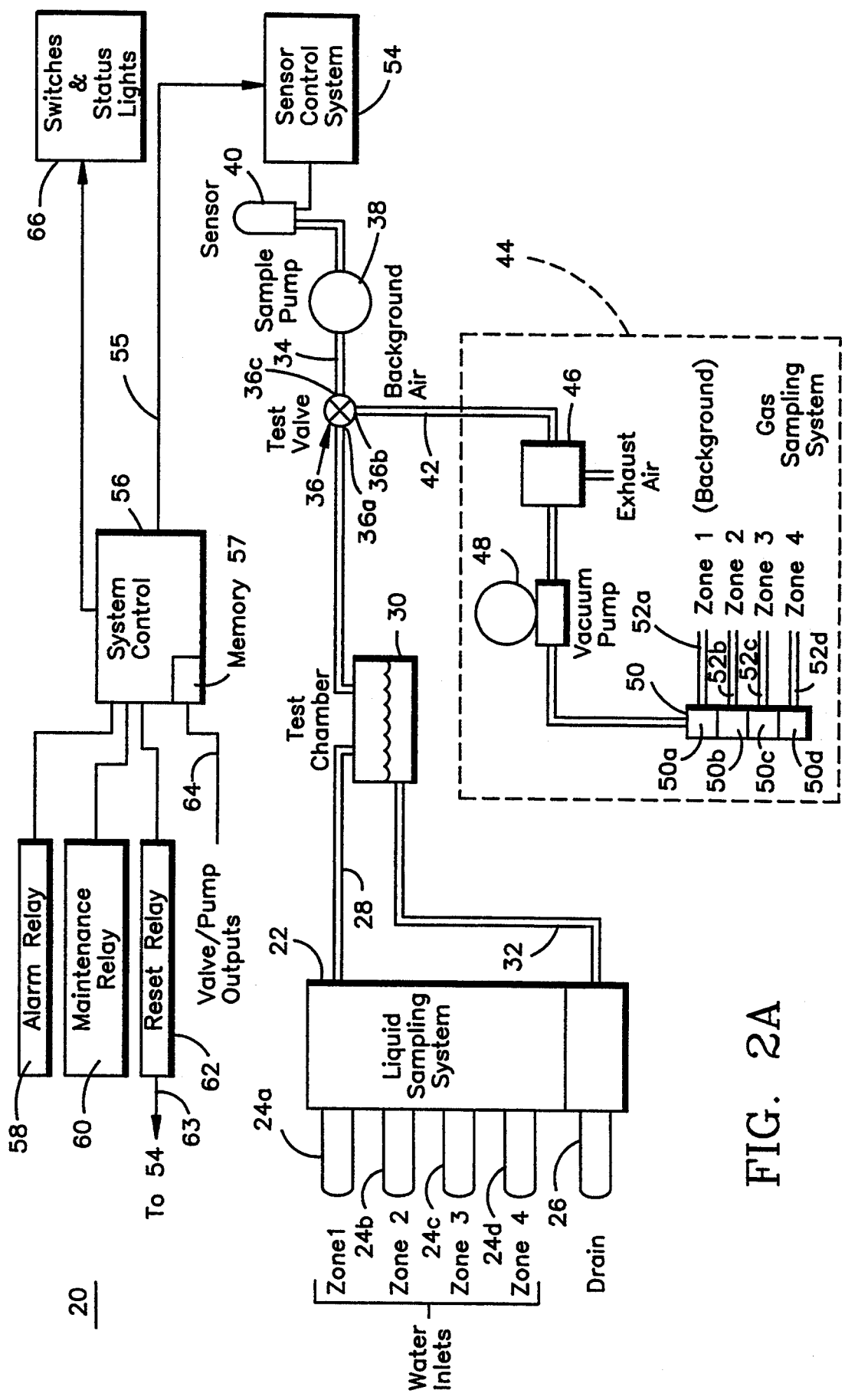
FIGS. 2A and B are respectively a general and a more detailed functional block diagram of a fluid sampling and detecting system in accordance with the teachings of this invention.

Referring now to the drawings and in particular to FIG. 2A, there is shown a fluid sampling and detecting system 20, which is capable of taking samples including a fluid and test gas, e.g., one of the halogen refrigerants, separating the test gas from the fluid and of monitoring the separated test gas to detect the presence of a particular gas of a concentration above a predetermined threshold level, and, if present, to actuate an alarm. It is appreciated that the term fluid includes both gases and liquids. In an illustratively embodiment of this invention as shown in FIG. 2A, there is disclosed a liquid sampling system 22 for taking gas/liquid samples drawn from each of a plurality of liquid zones or sources and a gas sampling system 44 for taking gas/gas samples drawn from one of a plurality of gas zones or sources. The liquid sampling system 22 includes a plurality of inlets or ports 24a-d, each of which is coupled to take a liquid/gas sample from a corresponding one of the plurality of liquid zones. Those liquid zones may in an illustrative embodiment of this invention be condensers 12 of the refrigeration system 10, which are connected by corresponding liquid interconnecting conduits 18a-d to the ports 24a-d. By such an arrangement, a plurality of refrigeration systems 10 may be monitored to detect the leakage of a refrigerant into their circulating water.

The liquid/gas sample from each such refrigeration system 10 is coupled one at a time to be directed via a fill hose or conduit 28 to introduce a series of the liquid/gas samples into a test chamber 30. The test chamber 30 operates to separate the gas from the liquid/gas sample and to transport the separated gas via a test gas conduit 34 to a sensor 40. After the gas is separated from the liquid/gas sample, the sample is discharged from the test chamber 30 via a drain conduit 32 to a drain port 26. A sample pump 38 conveys the separated gas from the test chamber 30 via the conduit 34 to the sensor 40. In an illustratively embodiment of this invention, where the gas to be detected is halogen, sensor 40 may take the form of that halogen sensor described in U.S. Pat. No. 4,910,463. It is appreciated that this invention is not limited to detecting only halogen gases and, accordingly, other sensors which are capable of detecting other gases may be included within the fluid sampling and detecting system 20 of this invention.

Still referring to FIG. 2A, there is shown a test valve 36 inserted within the test gas conduit 34. The test valve 36 is a three-way valve with a first outlet 36a in communication with the test chamber 30, a second outlet 36b communicating with the gas sampling system 44 via a background gas conduit 42 and a third outlet 36c communicating with the sensor 40 via the test gas conduit 34. The test valve 36 is actuated or energized from a first position connecting the background gas conduit 42 into communication with the test gas conduit 34, to a second position placing the test chamber 30 into communication with the test gas conduit 34. In the illustrative embodiment of this invention shown in FIG. 2A, the background gas conduit 42 is coupled to the gas sampling system 44. In an alternative embodiment of this invention, the gas sampling system 44 may be deleted and the conduit 42 merely be opened to sample the ambient or background gas. The gas sampling system 44 includes a junction 46 coupled to the conduit 42 for connecting the conduit 42 to a vacuum pump 48 and also to exhaust gas. In turn, the vacuum pump 48 is connected to a manifold 50 to draw air therefrom and to a selected one of a plurality of zones or sources through a corresponding one of the input inlets or ports 52a-d. Each of the ports 52a-d is coupled to a corresponding one of a plurality of gas zone solenoid valves 50a-d, which together comprise the manifold 50. Only one of the valves 50a-d is actuated at a time to couple a selected one gas zone to the sensor 40.

An output of the sensor 40 is connected to a sensor control system 54, which basically senses the amplitude of the sensor output signal with respect to a threshold level and, if above, provides an alarm output signal. More specifically, the sensor 40 responds to a concentration of the gas released from the test chamber 30 and, if above a predetermined concentration level provides its output signal via an electrical path 55 to a system control 56. The system control 56 applies output signal via a plurality of conductive paths collectively identified in FIG. 2A by the numeral 64, to the liquid sampling system 22 and the gas sampling system 44 to control which of the plurality of their valves is activated. Further, the control system 56 selectively actuates the test chamber 30, the test valve 36 and the sample pump 38 as will be described. The system control 56 also responds to the presence of a concentration of the test gas above the threshold level to actuate an alarm relay 58, which further energizes a status light to alert the operator as to which zone (gas or liquid) in which the leak was detected. The system control 56 also responds to an alarm signal from the sensor control system 54 indicating the presence of a concentration of the test gas above the preset threshold level, to actuate a reset relay 62 after a time period sufficient to permit either the liquid sampling system 22 or the gas sampling system 44 to reconnect the next inlet or port thereof to the sensor 40. Further, the system control 56 conducts various tests on the valves and pumps within the system 20 and, if found to be defective, sets the maintenance relay 60 whereby power is removed from the system 20 and the alarm relay 58 to actuate an alarm whereby an operator is made aware of these failures. The system control 56 is also connected to a control panel 66 which includes a plurality of switches and status lights.

Figure 2B:
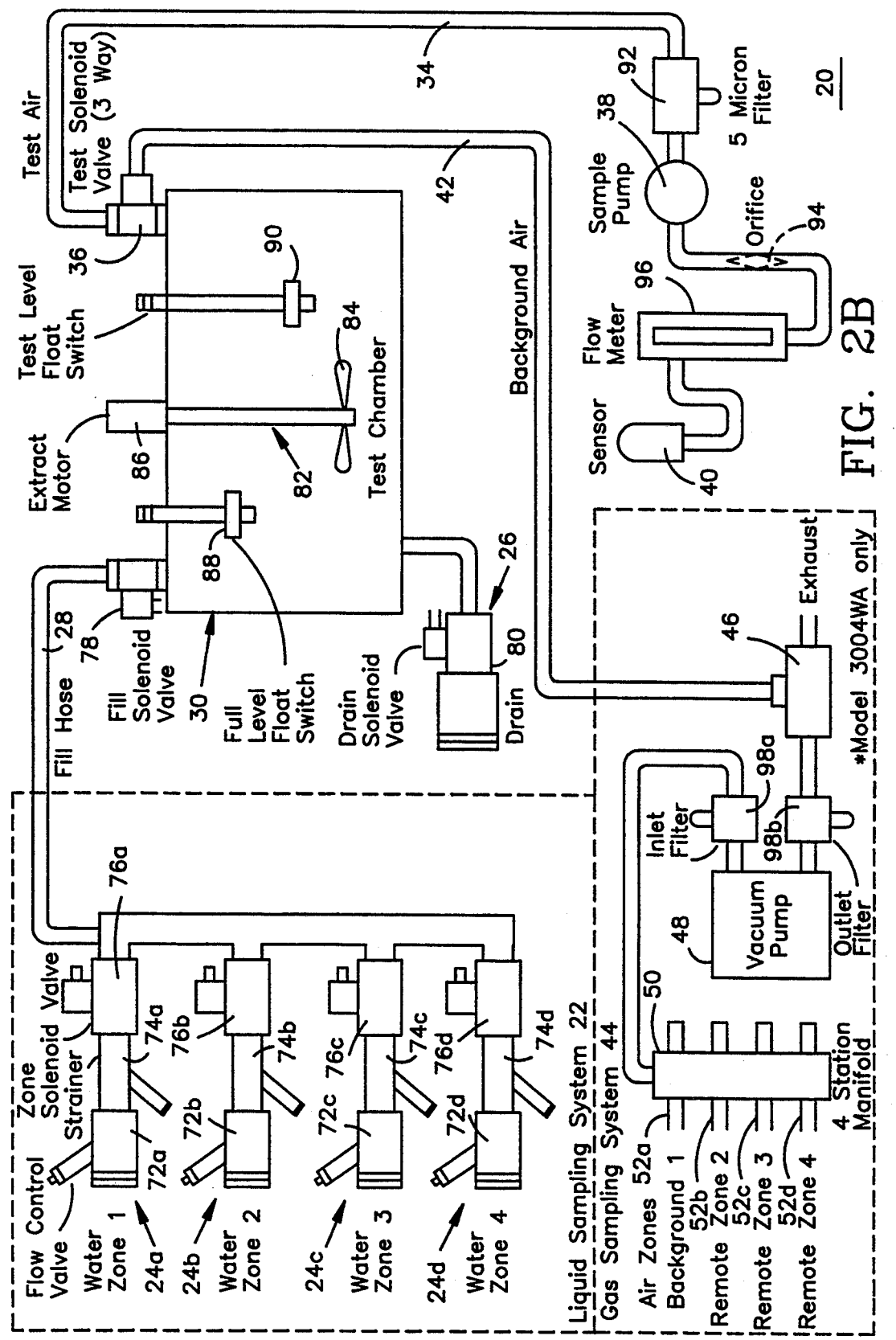

Referring now to FIG. 2B, further details of the elements and structure of the fluid sampling and detecting system 20 are shown. In the liquid sampling system 22, each of the plurality of ports 24a-24d includes a flow control valve 72, a strainer 74 and a liquid zone solenoid valve 76. Each strainer 74 traps particles which are conveyed in the liquid/gas sample from its liquid zone. The output pressure of the condensers 12, which are respectively connected to the ports 24a-d, may significantly vary, e.g., from 10-150 PSI. The flow control valves 72 insure that the flow rates of the samples through each of the ports 24a-d, the fill conduit 28 and into the test chamber 30, remain substantially constant. Otherwise, if samples were introduced into the test chamber 30 at different rates, some of the samples may be splashed into the test air conduit 34 and have a deleterious effect on the operation of the sensor 40. In addition, there will be different degrees of agitation of the test sample and thus the percentage of the gas released from the sample may differ, if the flow rate at which samples are introduced into the test chamber 30 varies. The common flow rate is set sufficiently low to insure that as the samples are introduced into the test chamber 30, there is no splashing. Maintenance may be required to clean and to remove the particle from its strainer 74 to prevent a decrease of the mixture flow to the test chamber 30. Each solenoid valve 76 is energizable from a closed position to an open position. In the closed position, each valve 76 prevents the flow of the liquid/gas sample from its liquid zone and in its open position, permits the flow of the sample from its liquid zone via the fill hose or conduit 28 to the test chamber 30. As will be explained, the system control 56 provides a signal via a corresponding one of the conductor paths 64 to each of the zone solenoid valve 76a-d to selectively dispose only one valve 76 to its open position, whereby the fluid/gas sample from a selected one liquid zone may be drawn by the sample pump 38 to the test chamber 30.

The fill conduit 28 conveys the liquid/gas sample from the selected liquid zone via a fill solenoid valve 78 into the test chamber 30. The amount of the sample introduced into the test chamber 30 is controlled by a full level float switch 88 and a test level float switch 90. As the level of the sample rises in the test chamber 30, it will first actuate the test level float switch 90 and then the full level float switch 88. The height of the test level float switch 90 within the test chamber 30, defines a fixed quantity of the liquid/gas sample. As will be explained, the introduction of each liquid/gas sample from the different liquid zones is controlled, i.e., the level of the sample within the test chamber 30 actuates the test level float switch 90, whereby the fill solenoid valve 78 is deenergized and closed. Thus, each liquid/gas sample is of the same quantity and volume, whereby the measurements of the released gas from samples of a predetermined quantity are made consistent. If samples of different volume were introduced in the test chamber 30, the measurements by the sensor 40 of the released gas would vary accordingly. The position of the full level float switch 88 defines an amount of the sample that is drained into the test chamber to flush or cleanse the liquid sampling system 22, the fill conduit 28 and the test chamber 30, before it is discharged through a drain port 26. The drain port 26 is coupled to a drain solenoid valve 80, which is actuated from a closed position to an open position to permit the sample introduced into the test chamber 30 to be discharged or drained therefrom.

An agitator 82 is mounted on the test chamber 30 to physically agitate the liquid/gas sample, whereby the gas captured within the sample in the form of bubbles is released into an upper portion of the test chamber 30 above the sample. As shown in FIG. 2B, the agitator 82 includes an extract motor 86 and a propeller 84, which in one illustrative embodiment of this invention may take the form of a Labmaster MS Mixer. The rotating propeller 84 agitates the sample, whereby the gas captured within the sample is released. It is believed that the gas and, in particular, the refrigerant is captured within the liquid, e.g., water, as bubbles and entrained within the water. The rotating propeller 84 agitates or breaks up the bubbles releasing them from the sample and into that open volume above the sample within the test chamber 30. It is significant that the same amount of agitation is provided to each sample. This is accomplished in this illustrative embodiment where a rotating propeller 84 is employed, by energizing its extract motor 86 for a fixed period of time for each sample, e.g., 3 minutes. Though agitation is provided in this example by a rotatively driven propeller 84, it is contemplated that other means of agitation such as shaking the test chamber 30 in the manner of a paint mixer, directing a sequence of pulses of the sample into the test chamber 30 or directing a stream of bubbles through the test chamber 30 would also provide the desired agitation.

The discharge of the released gas from the test chamber 30 is controlled by the test solenoid valve 36, which is energizable from a first position to a second position by a signal outputted from the system control 56. In its first position, the test solenoid valve 36 seals the test chamber 30 to prevent the escape of the released gas therefrom, and interconnects the background gas conduit 42 to the test air conduit 34 whereby a gas/gas sample from a selected gas zone or the background may be drawn by the vacuum pump 48 to the sensor 40. The vacuum pump 48 remains energized throughout the liquid test cycle and is only deenergized when the control system 56 is disposed in its maintenance mode. In its second energized position, the test solenoid valve 36 blocks the background gas conduit 42 and interconnects the test chamber 30 and the test air conduit 34, whereby the released gas from the sample may be conveyed by the sample pump 38 to the sensor 40. The test gas conduit 34 conveys the separated gas via a fine particle filter 92, the sample pump 38, an orifice 94 and a flow meter 96 to the sensor 40. The fine filter 92 removes small particles which may be otherwise entrained within the conveyed gas. The orifice 94 insures that a constant flow rate of the released test gas is drawn to the sensor 40 for each sample introduced into fluid sampling and detecting system 20. The sensor 40 as illustratively disclosed in U.S. Pat. No. 4,910,463 is sensitive to the flow rate at which gases are directed thereto. In an illustrative embodiment of this invention, the orifice 94 is configured to provide a fixed flow rate of the released gas in the range of 300–400 cc/minute. The flow meter 96 displays the flow rate, so that the operator can verify that the flow rate of the released gas to the sensor 40 is constant.

The gas sampling system 44 employs the vacuum pump 48 to draw the gas/gas sample through a selected one of the ports 52$a$–$d$. The manifold 50 includes the plurality of corresponding zone solenoid valves 50$a$–$d$, whereby the continuous energized vacuum pump 48 draws the gas/gas sample from the selected one zone through the energized one of the valves 50$a$–$d$ via an inlet filter 98$a$, the vacuum pump 48, an outlet filter 98$b$, the junction 46, the background gas conduit 42 and the test gas conduit 34 to the sensor 40. The vacuum pump 48 has a high flow rating, e.g., 40 liters/minute, to be able to draw gas/gas samples from remote gas zones through hundreds of feet of interconnecting conduits. If the output of the vacuum pump 48 were directly connected through the conduits 42 and 34 to the sensor 40, the sensor 40 may be damaged by such high flow rates. Therefore, the junction 46 is inserted to exhaust most of the vacuum pump output, while permitting a relatively small, safe flow rate through the conduits 42 and 34 to the sensor 40. The inlet filter 98$a$ protects the vacuum pump 48 from particles which may be drawn from a coupled gas zone. The first port 52$a$ of the manifold 50 is in communication with the ambient or background air or gas surrounding the fluid sampling and detecting system 20. The background gas is periodically sampled immediately before taking each liquid/gas sample from one of the liquid zones to determine the presence of the test gas and, if present, to provide a warning that the subsequent sampling and detection of the liquid/gas samples may be contaminated by the presence of the test gas in the background air about the system 20. In the absence of the gas sampling system 44, the background air conduit 42 would be open to the background or ambient gas to permit periodic samplings as will be described.

Figure 3A:
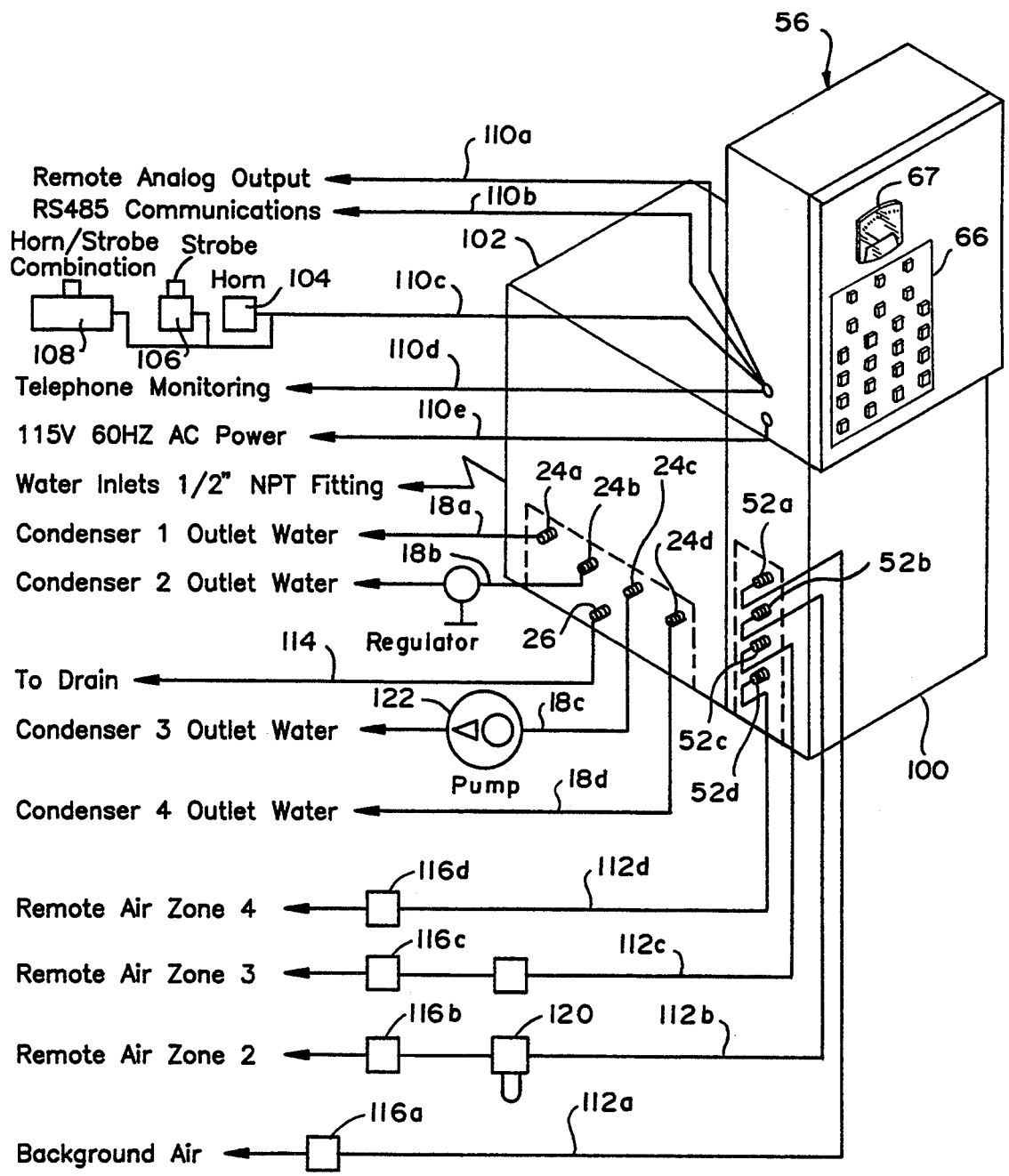
FIGS. 3A and B are respectively a perspective view of the system control and the housings for the gas and liquid sampling systems and the respective fluid and electrical connections to the components of this invention, and a control panel of the system control.

Referring now to FIG. 3A, there is shown the system control 56 having a control panel 66 and a display 67 of the concentration of the gas illustratively in parts per million (PPM). A power line 110$e$ connects power to the control 56. Since the fluid sampling and detecting system 20 continuously monitors for the presence of a particular test gas of a concentration above the threshold level, it is preferred that the line 110$e$ be permanently connected to the AC power so that the system control 56 may not be unplugged. Electrical conduit 110$c$ is connected to the alarm relay 58, which when set serves to energize an alarm horn 104, or a strobe light 106 or a combination of a horn and strobe 108. Electrical conduit 110a provides an analog output to a remote display for providing an indication of the concentration level of the detected test gas. Electrical conduit 110b provides via an RS 485 communications interface an interconnection to a remote computer. Electrical conduit 110d provides a connection via a normal telephone system to a centrally disposed station, which can monitor a plurality of the systems 20.

A housing 102 encloses the liquid sampling system 22. The housing 102 supports the liquid input ports 24a-d, which are coupled via corresponding conduits 18a-d to their respective liquid zones, e.g., water outlets of distinct condensers 12. Drain port 26 is coupled by a drain conduit 114 to discharge the liquid/gas samples from the test chamber 30. If one of the conduits 18 is particularly long or otherwise has a relatively low pressure therein, it may be necessary to employ a liquid pump 122 to increase the flow pressure of that liquid/gas sample to its port 24.

A second housing 100 encloses the gas sampling system 44 and supports the corresponding gas input ports 52a-d. Corresponding of the ports 52a-d are connected to interconnecting gas conduits 112a-d to respective of the background air and the remote air or gas zones. Each of the conduits 112 may require a coarse filter 116 to remove particles otherwise conveyed from the remote air or gas/gas zones to the sensor 40. A further filter such as a filter separator assembly 120 may be disposed in those conduits 112, which are connected to a particularly dirty environment to make sure that all of the particles are trapped before reaching the gas sampling system 44 or the sensor 40.

Figure 3B:
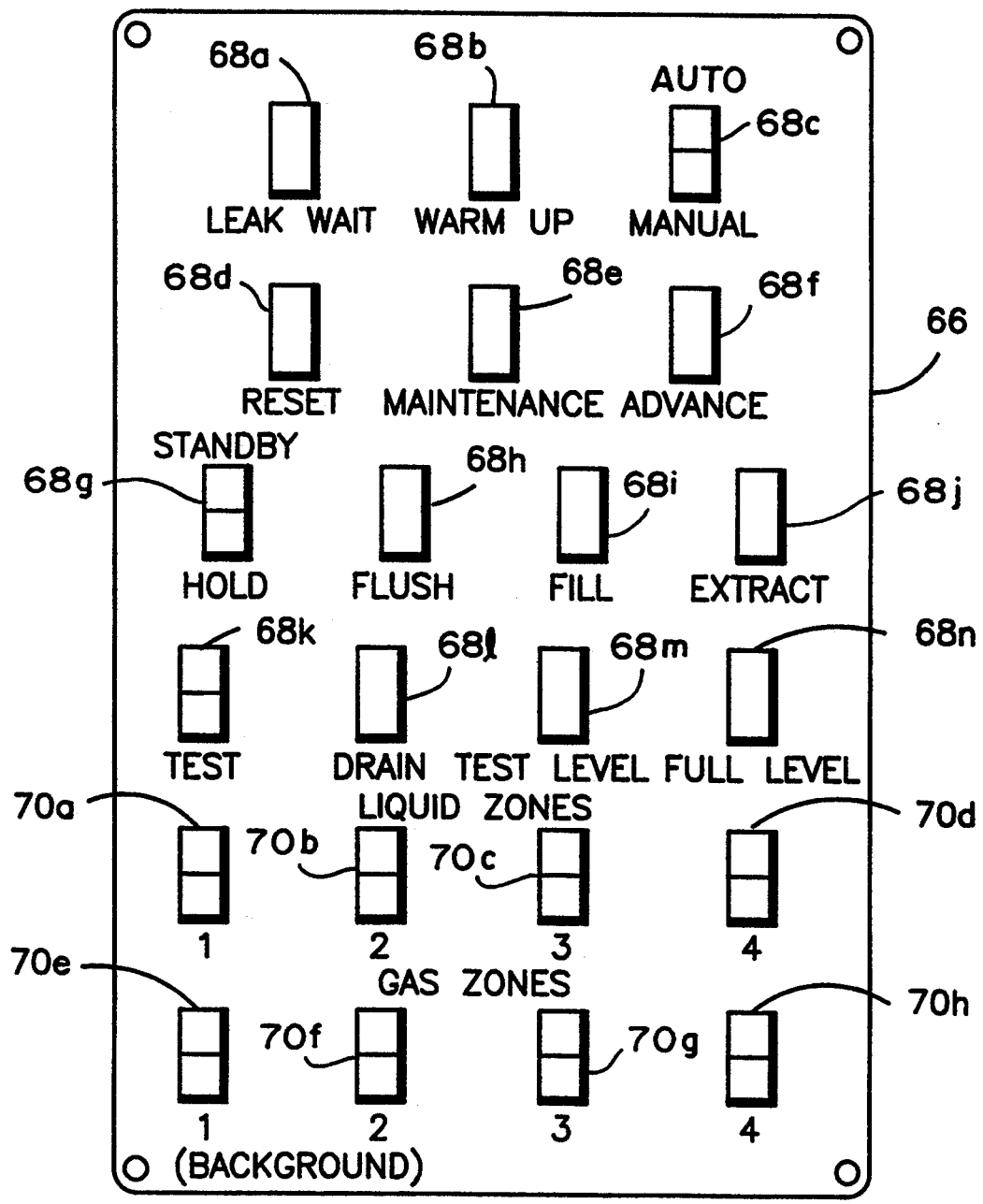

In FIG. 3B, there is shown a control panel 66 bearing switches or lights 68 and status lights 70. A switch 68c permits the operator to operate the system control 56 in either an automatic or manual mode. The manual mode is used for confirming reported leaks, for making certain that they have been corrected and for trouble shooting the equipment. In the manual mode, the system control 56 keeps only one of the liquid zone solenoid valves 76 associated with the liquid sampling system 22 or one of the valves 50 associated with the gas sampling system 44 energized and opened. To move from one zone to the next, it is necessary to actuate the standby switch 68g and then depress the advance switch 68f. In the manual mode, each of the various steps of introducing and discharging the liquid/gas sample to and from the test chamber 30 can be individually selected by actuating a corresponding one of the flush switch 68h, the fill switch 68i, the extract switch 68j, the test switch 68k and the drain switch 68l. The operation of the system 20 can be manually completed through a complete cycle by sequentially actuating the switches 68h-l to double check that there is a leak condition. If there is a concentration of the released test gas in excess of the threshold level, the sensor control system 54 will first provide a leak wait signal and then possibly an alarm signal. However, unlike the automatic mode, the system control 56 will not automatically reset itself and cause the system to sample the next zone.

The system control 56 responds to the leak wait signal from the sensor control system 54 to energize the leak wait light 68a during the leak wait mode and at no other time. The leak wait mode is established by the sensor control system 54 for a period during which the system 54 determines whether the output of the sensor 40 and therefore the concentration level of the sensed gas is above the threshold level to prevent the false sensing of extraneous signals. The warm-up light 68b is energized during the warm-up period and at no other time. As will be explained, the sensor 40 is energized for a sufficient time to permit its elements to be heated and to stabilize at an operating condition before the sensor 40 is called on to monitor the released gas. A reset switch 68d resets the alarm relay 58 and the maintenance relay 60 and causes the sensor control system 54 to return to its warm-up mode. The maintenance switch 68e provides a dual function. It is back lit to provide an indication that a pump or valve failure has occurred or that a high concentration of the test gas has been detected in all zones or in the background air (or gas) and are in alarm. When the maintenance switch 68e is depressed, the alarm relay 58 is momentarily energized and all zone alarm lights 70 are lit and the alarms 104, 106 and 108 are actuated. This provides a means of testing the horn 104, the strobe 106 and the combination horn/strobe 108. The standby/hold switch 68g may be actuated to select the standby mode when the system control 56 is in its manual mode. The switch 68g has a standby light and a hold light; the standby light may be energized to indicate that the system control 56 is in the standby mode and the hold light indicates that the cycle repeat timing sequence is active. The flush switch 68h is actuated to cause a corresponding one of the ports and its interconnecting conduit to be flushed when the system control 56 is in its manual mode. The fill switch 68i allows operation in the fill step when the system control 56 is in its manual mode to permit the test chamber 30 to be filled. The extract switch 68j is actuated when the system control is in its manual mode to energized the agitator 82 and its extract motor 86. The test switch 68k is actuated when the system control is in its manual mode to open the test valve 36 and to energize the sensor control system 54 and its sensor 40. The test level light 68m and the full level light 68n indicate that the liquid has filled the test chamber 30 to the corresponding test and full levels, thus closing the switches 90 and 88. Each of the zone lights 70 has a green light and a red light. An energized green light indicates that a corresponding zone has been selected to be connected by its valve to the system 20. The red light indicate that an alarm signal has been received from the sensor control system 54 and a high concentration of the test gas has been sensed in that zone.

Figure 4A:
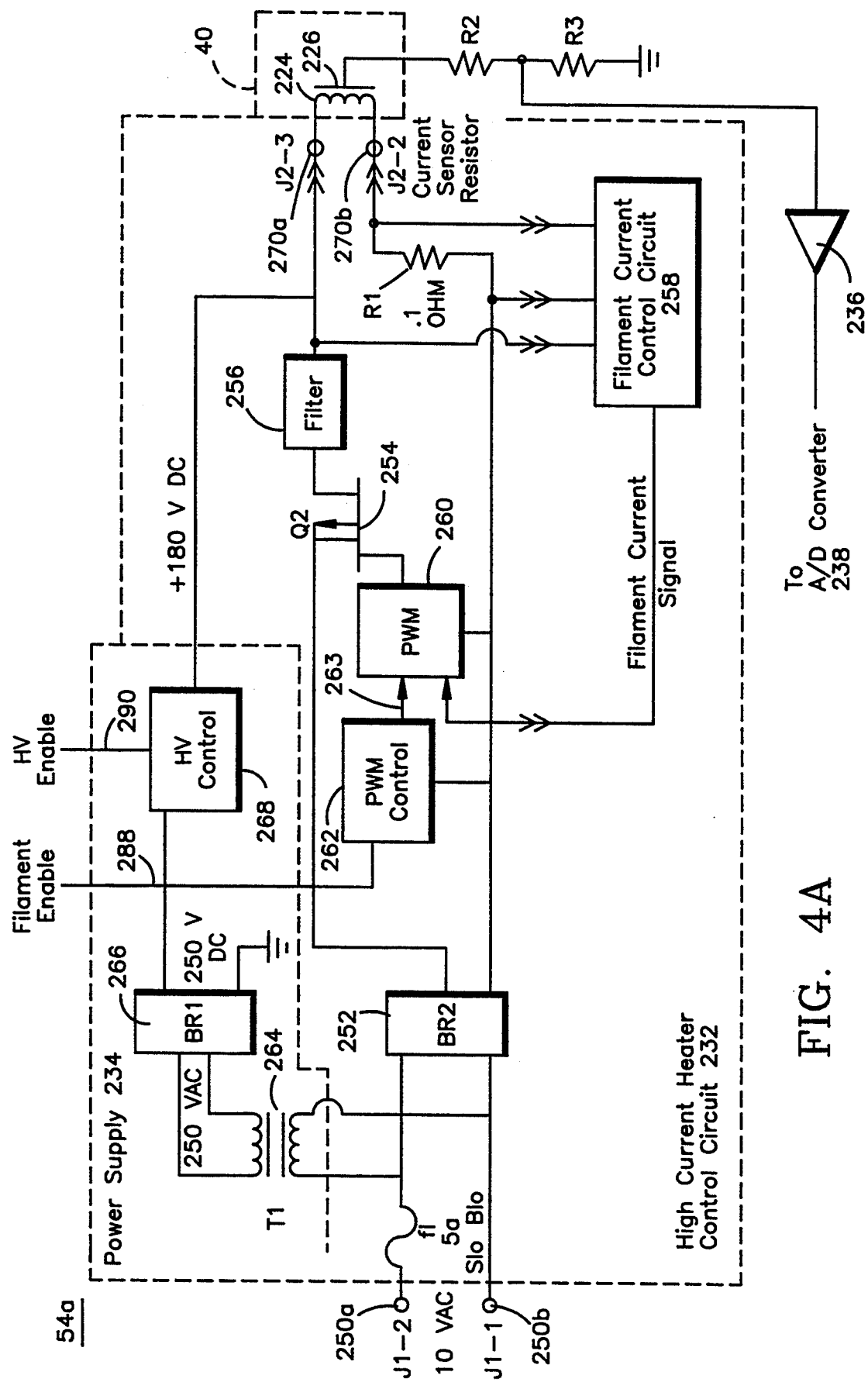
FIGS. 4A and B are respectively functional block diagrams of the sensor power circuit and the sensor digital control circuit, which comprise together the sensor control system shown in FIG. 2A.
Figure 4B:
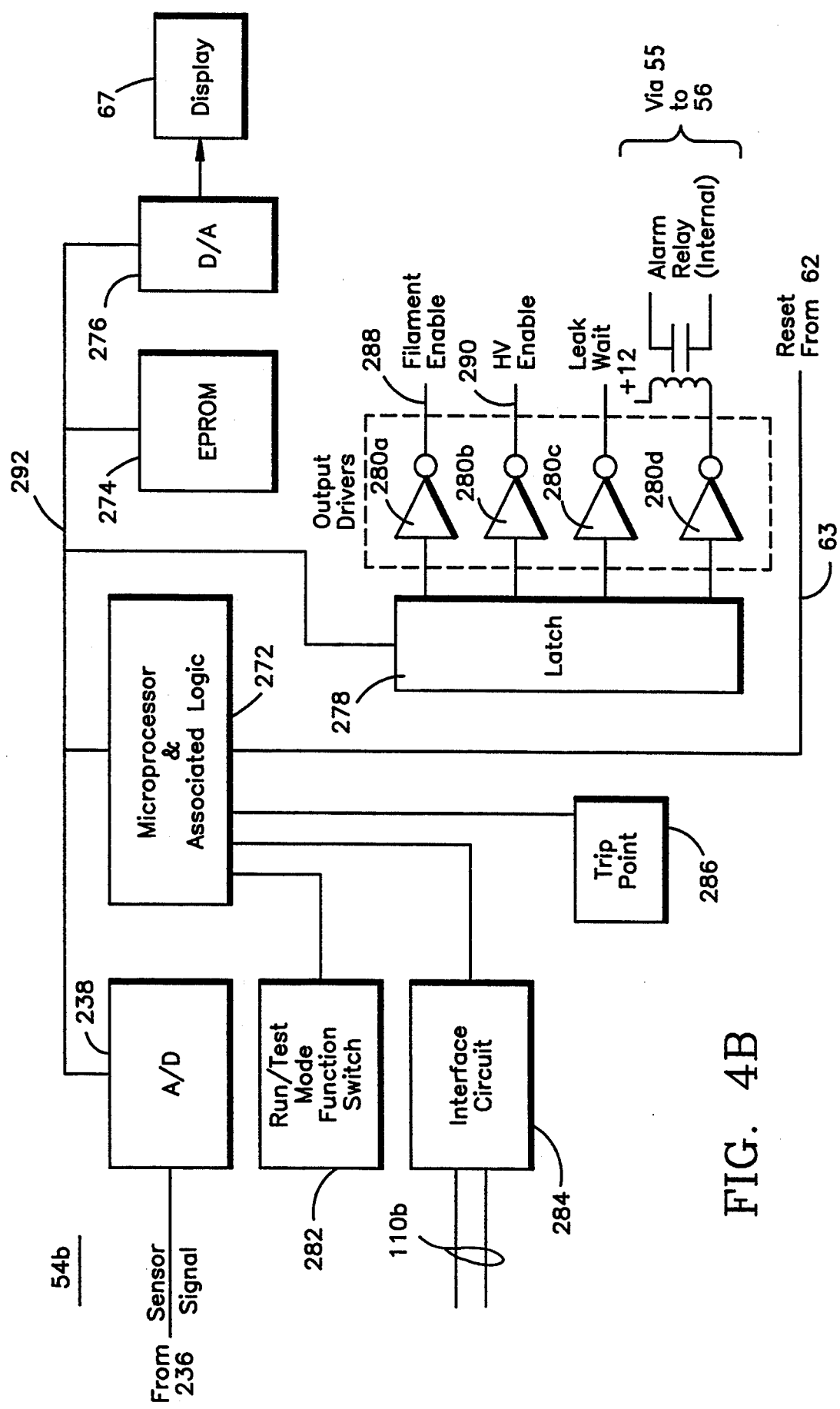

The sensor control system 54 shown in FIG. 2A comprises a sensor power control system 54a shown in FIG. 4A and a sensor processing circuit 54b shown in FIG. 4B. Referring now to FIG. 4A, there is disclosed the structure and operation of the sensor 40 and the sensor power circuit 54a for energizing the sensor 40. The sensor 40 is adapted in an illustrative embodiment of this invention to sense halogens and, to that end, is adapted to heat the sample of the released test gas drawn into the sensor 40 from the test gas conduit 34 to a temperature of approximately 900° C. The sensor 40 comprises a collector/cathode element 226 and a heater/anode element 224, which are spaced apart to define a space through which the released test gas is drawn. The heater/anode element 224 is energized to heat the separated test gas to a temperature, which ionizes any halogen based hydrocarbons present in the test gas. A relatively negative voltage is established upon the collector/cathode element 226 of the sensor 40, thus attracting any positively charged halogen ions thereto and establishing a small current ion flow, which is applied, as shown in FIG. 4B, to a sensor input of the sensor processing circuit 54b. The amplitude of that ion current is proportional to the relative concentration of the halogen gas in the separated test gas. The sensor power circuit 54a applies a voltage across the heater-/anode element 224, which heats the test gas to the desired temperature. In an illustrative embodiment of this invention, the gas sensor 40 may take the form of that sensor manufactured by Yokagowa Corp. under its designation 6614K11G1. The collector/cathode element 226 thereof illustratively takes the form of a rod suspended in a powdered-alkaline metal core housed in a concentric platinum tube. The tube and rod are connected by a welded platinum strip, thus keeping rod and tube at the same potential. The heater/anode element 224 may illustratively take the form of a coiled/wire or filament, which is wrapped about four ceramic posts and disposed about the aforementioned rod/tube assembly. The filament is made of a material, e.g., platinum, whose impedance (resistance) is variably dependent upon its temperature and thus the temperature of the gaseous atmosphere directed thereby. The temperature dependent property of the anode's filament is used as will be described below to control its energization. Illustratively, a voltage in the order of a 180 volts is imposed between the heater/anode element 224 and its collector/cathode element 226. Approximately 4 volts is applied across the heater/anode element 224, whereby current in a normal range of 3.5 to 4 amps is directed therethrough and the temperature of the gas sensor 40 is raised to approximately 900° C., causing the ion current to flow in the rod of the collector/cathode element 226. Though an illustrative sensor has been described, it will be appreciated that other sensors may be incorporated into the sensor control system 54 to sense other gases without departing from the teachings of this invention.

The sensor power circuit 54a includes a current heater control circuit 232, which measures the impedance, e.g., resistance, of the filament forming the heater/anode element 224 to thereby sense the element's temperature and thus the temperature of the sampled test gas. As will be explained, that sensed filament resistance is used to control the current, typically in the range of 3.5 to 4 amps, which is applied to the heater-/anode element 224, whereby the filament current and therefore its temperature are precisely controlled.

The sensor power circuit 54a also includes a power supply 234, which controls the application of the relatively high voltage, e.g., 180 V DC, across the heater-/anode element 224 and the collector/cathode element 226 of the gas sensor 40. The power supply 234 comprises a transformer 264, whose primary winding is coupled via the fuse f1 to the voltage input terminals 250a and 250b, whereby a relatively low alternating voltage, e.g., 10 V AC, is increased to a relatively high level, e.g., 250 V AC. The relatively high voltage is applied to a bridge 266 to output therefrom a DC voltage. The application of that DC voltage is controlled by a high voltage (HV) control circuit or switch 268, whereby that high voltage may be selectively applied and removed from the sensor 40 and in particular from across its elements 224 and 226. As will be explained, the sensor processing circuit 54b applies an enable signal via a high voltage enable line 290 to the HV control circuit 268 to apply and to remove the high voltage from the sensor 40. For example, when the presence of the test gas of a concentration above the preset level has been sensed, the HV control circuit 268 may be disabled to remove the voltage from across the elements 224 and 226 of the sensor 40 and thus preserve the life of the sensor 40.

The current heater control circuit 232 comprises a bridge 252 coupled to an input power source, e.g., 10 V AC, via a fuse F1 to provide DC power to the current heater control circuit 232. The selective application of the DC output voltage of the bridge 252 is controlled by a power switch in the form of a power transistor 254, which is selectively turned on and off by a pulse width modulator (PWM) 260, whereby a sequence of pulses is outputted from the transistor 254. In turn, these pulses are smoothed by a filter 256 before being applied via filament output terminals 270a and b across the heater-/anode element 224. The filter 256 "smooths out" or filters the series of pulses, whereby a DC current of selected amplitude is applied through the filament comprising the heater/anode element 224.

The current amplitude applied to the heater/anode element 224 is controlled proportionately to the amplitude of an error signal output by a filament current control circuit 258, which is coupled to the heater-/anode element 224 to sense its resistance and therefore its temperature. The circuit 258 responds thereto to apply its error signal to the pulse width modulator (PWM) 260, whereby the power transistor 254 is turned on and off at a controlled pulse width rate and its filtered output is of a controlled current amplitude to maintain the current and therefore the temperature of the element 224 at a precise level. It is appreciated that the temperature of the released test gas to be monitored may vary and that consequently the temperature of the sampled test gas drawn into the sensor 40 may likewise change. This invention appreciates that changes of atmosphere or background gas temperature, as well as the rate of the atmosphere flow through the sensor 40, effect the temperature of the heater/anode element 224 and that, in turn, the filament temperature changes or drifts may cause corresponding errors in the amplitude of the collected ionization current which are independent of the test gas concentration to be detected. The heater/anode element 224 is typically a platinum wire, which has the desired characteristic of acting as an accurate temperature sensor, i.e., its resistance accurately reflects its temperature. Thus to compensate for changes or drifts in the sampled environment temperature and any fluctuations of the environment flow rate thereof through the sensor 40, the difference between the resistance of the element 224 and a reference value is sensed by the filament current control circuit 258 to thereby proportionately control the amplitude of the current flowing through and therefore the temperature of the element 224. This proportionate control of the amplitude of the current applied to the heater anode element 224 achieves a closer, more accurate control of the heater/anode element temperature than achieved by increasing the element current by a fixed amount. Thus, the amplitude of the output signal from the sensor 40 is a more accurate indication of the concentration level of the detected gas. A more detailed description of the sensor 40 and the filament control circuit 258 is found in the above referenced, co-pending application entitled, "Method and Apparatus for Monitoring for the Presence of a Gas".

Further, the current heater control circuit 232 includes a pulse width modulation (PWM) logic circuit 262, which is responsive to an enable signal applied via a filament enable line 288 from the sensor processing circuit 54b of FIG. 4B, to selectively turn on and off the power transistor 254, whereby the relatively high levels of current may be removed from the filament comprising heater/anode element 224. As will be described below, upon sensing the presence of a gas and in particular a halogen gas of a concentration above the threshold level or set point, the gas sensor 40 is deactivated, whereby the flow of halogen ions to the collector/cathode element 226 is stopped and the life of the gas sensor 40 prolonged.

Further, the PWM logic circuit 262 provides a current limiting signal via line 263 to the pulse width modulator 260 to provide protection during a warm-up mode. When the sensor 40 and it's elements 224 and 226 are relatively cool, the current applied to the filament of the heater/anode element 224 is limited to a maximum amplitude, e.g., 5 amps. Once the sensor 40 and it's element 224 and 226 have warmed up, the microprocessor 272 permits the current applied to the element 224 to be set in its normal range, e.g., 3.5 to 4 amps. In the warm-up mode, the collector/cathode element 226 is relatively cold and its resistance relatively low. Thus, if the current supply to the heater/anode element 224 were not appropriately controlled by the pulse width modulator 260, the current drawn from the collector/cathode element 226 may surge quickly to a magnitude, which would destroy the elements of the sensor control system 54 and, in particular, the power transistor 254.

After the warm-up mode has expired, the sensor processing circuit 54b applies an enable signal via the high voltage enable line 290 to the high voltage control circuit 268, which is closed thereby to permit a high voltage to be applied across the heater/anode element 224 and the collector/cathode element 226. As a result, a signal current is drawn from the element 226 through a voltage divider network comprised of resistors R2 and R3. The voltage across resistor R3 is buffered by an analog amplifier 236, which is a unity gain amplifier, before being applied to the analog-to-digital converter 238 of the sensor processing circuit 54b, as shown in FIG. 4B. When the sensor 40 is relatively cool, the resistance of the filament comprising the element 224 is relatively low, so that current is limited to a maximum of 5 amps as described above. After the warm-up period, the sensor 40 is operated so that current applied to the heater/anode element 224 lies in a normal range, e.g., 3.5 to 4 amps. The sensor output drawn from the collector/cathode element 226 varies in a range from 0.1 volts or less when no gas is detected to a high of 1.5 volts at 100 PPM, when the system is calibrated in its calibration mode for 100 PPM full scale.

Figure 1:
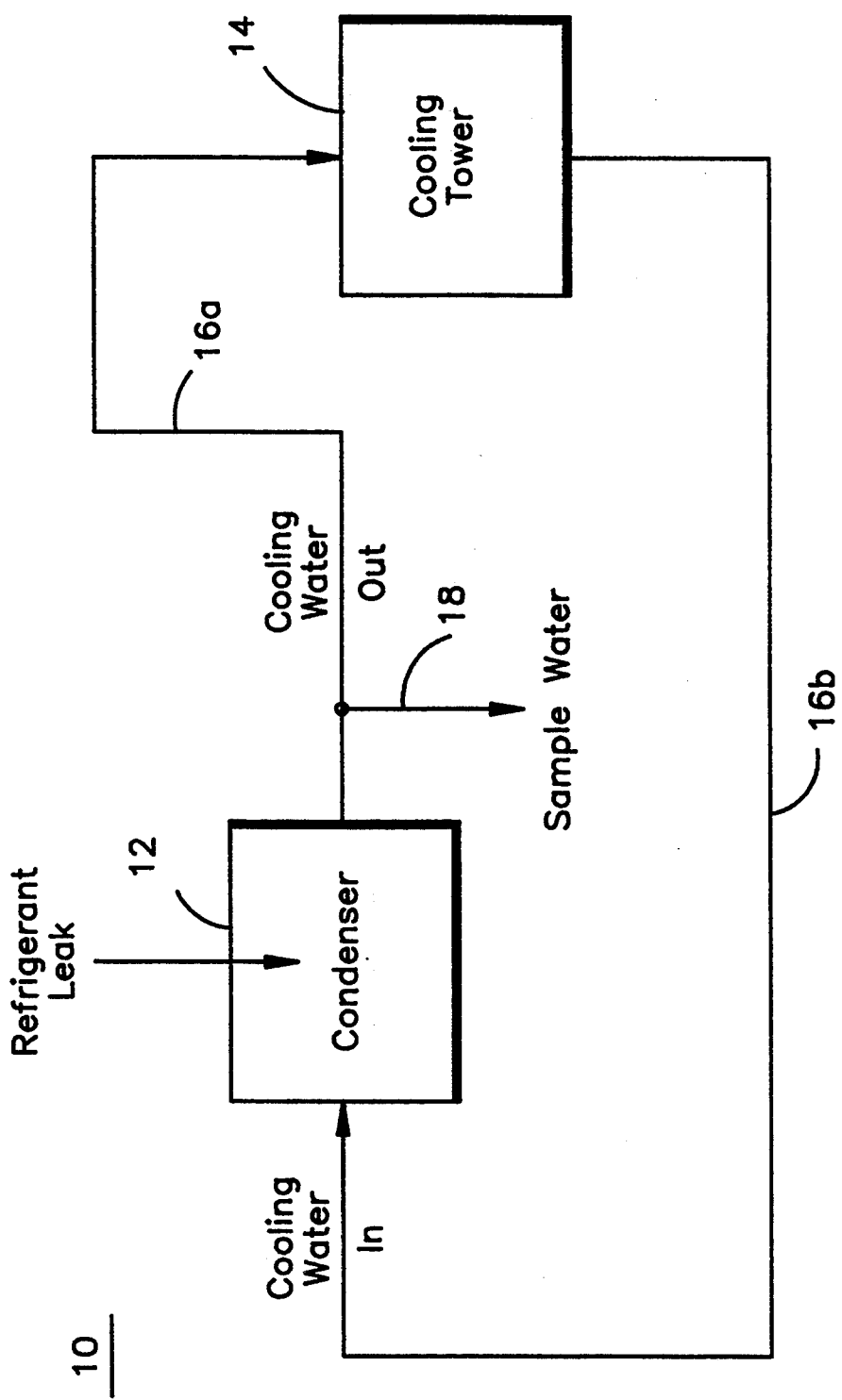
FIG. 1 is a schematic representation of a refrigeration system showing the circulation of cooling water subject to contamination by a refrigerant such as halogen which may leak from a condenser to a cooling tower and return.

Referring now to FIG. 4B, there is further shown the sensor processing circuit 54b, which is coupled to the collector/cathode element 226 to receive and process the ion current for providing on the display 67 an indication of the concentration of the detected test gas. The sensor processing circuit 54b comprises an analog amplifier circuit 236 for amplifying and applying the ion current received from the sensor 40 to the analog-to-digital converter 238, which converts the analog ion current signal to an output, which is a digital representation or word indicative of the amplitude of the ion current. In turn, that digital word is applied to a microprocessor 272, which processes that digital word to provide upon the display 67 an indication of the test gas concentration and to provide the alarm signal to the system control 56, whereby an alarm signal may be transmitted over the conductive path 110d and a conventional telephone system to a remote location. It is contemplated that a plurality of the fluid sampling and detecting systems 20, as shown in FIGS. 2A and 2B, may be disposed at a plurality of remote locations and that each could be coupled by a conventional telephone system with a centrally located monitoring station, whereby a single operator may monitor the presence or leaking of the test gas from a plurality of the condensers 12 as shown in FIG. 1, at corresponding remote locations. For example, a food chain could monitor its produce refrigeration systems 10 at each store of that chain from a single, centrally located station.

The microprocessor 272 is coupled via a data/address bus 292 to the analog-to-digital converter 238, whereby the ionization current as amplified by the analog amplifier 236 and converted to a digital word by the A/D converter 238 may be processed by the microprocessor 272, a memory in the form of an EPROM, a digital-to-analog converter 274 whereby the digital signals appearing on the bus 292 may be converted to corresponding analog signals, and a latch 278.

The sensor processing circuit 54b and the sensor 40 are capable of being operated in the following modes: warm-up, monitoring, test, leak-wait, alarm and calibration. The operator may manually set a run/test mode switch 282 in one of its corresponding positions, run or test, to thereby determine in which mode the sensor processing circuit 54b is to operate. When the sensor control system 54 is operating with the system control 56, the switch 282 is kept in its run position. A trip point set switch 286 is also coupled to the microprocessor 272, whereby the threshold level in terms of the concentration of the test gas to be detected, e.g., PPM of halogen gas, may be set. The microprocessor 272 processes the ionization current derived from the collector/cathode element 226 to determine whether the concentration of the test gas within the sensor 40 is above or below the threshold level by the switch 286. The microprocessor 272 may be further coupled by an interface circuit 284 and the conductive path 110b to a remote computer. The microcomputer 272 sets the latch 278 whereby outputs are developed from selected of a plurality of its output drivers 280a, 280b, 280c and 280d. As shown in FIG. 4B, the output of the output driver 280a provides an enable signal via the filament enable line 288 to control the PWM logic circuit 262 as shown in FIG. 4A. The output driver 280b applies an enable signal via the high voltage enable line 290 to the HV control circuit 268 as shown in FIG. 4A.

When the gas processing circuit 54a has sensed a test gas concentration above the threshold level and the leak wait mode has timed out, the microprocessor 272 enters its alarm mode. In the alarm mode, the output driver 280d applies the alarm signal via the conductive path 55 to the system control 56. In order to exit the alarm mode, the system control 56 of FIG. 2A actuates its reset relay 62, whereby a reset signal is applied via a conductive path 63 to the microprocessor 272.

The operation of the sensor control system 54 is controlled in accordance with a computer program, which is stored in the EPROM 274 as shown in FIG. 4B. The program controls which mode, i.e., warm-up, monitoring, test, leak-wait, alarm, or calibration, that the sensor processing circuit 54b is currently disposed and, further, controls accurately the current and therefore the temperature of the filament comprising the heater/anode element 224, whereby the accuracy of the output of the sensor processing circuit 54b in terms of the detected concentration level of gas is significantly improved. The following will describe briefly the operation of the sensor control system 54 in these modes as controlled by the program. A complete, detailed description of the operation of the sensor control system 54 in its various modes is found in the above identified co-pending application entitled, "Method and Apparatus for Monitoring for the Presence of a Gas".

Initially, after the run-test mode switch 82 is disposed to its run mode position, the sensor control system 54 is disposed in its warm-up mode. In the warm-up mode, a relatively high current is applied for a first predetermined period to the heater/anode element 224 without applying a voltage between heater/anode element 224 and the collector/cathode element 226. After the first period has timed out, the warm-up mode then applies the high voltage between the elements 224 and 226 for a second period, which is set typically shorter than that of the first period to permit any ions generated during the first period to be collected and the resulting transient peaks in the collected ion current to die out before operating in the next mode, i.e., the monitoring mode. In the warm-up mode as shown in FIG. 4B, the latch 278 is actuated and it's output driver 280a applies a filament enable signal via line 288 to the PWM logic circuit 262 of FIG. 4A, whereby the pulse width modulator 260 and the power transistor 254 are enabled to apply a relatively high current through the filament of the heater/anode element 224 and to set a count into a first or filament current counter. Next that counter is decremented to time this first period. After the first or filament current period has timed out, e.g., 2.5 minutes, the timing of a second or high voltage period is begun by actuating the latch 278 of FIG. 4B and it's output driver 280b to apply a high voltage enable signal via line 290 to the HV control 268 of FIG. 4A, whereby a high voltage in the order of 180 V DC is applied across the elements 224 and 226 of the sensor 40, and sets a count within a high voltage period counter. As a result, a current begins to be drawn from the collector/cathode element 226 and is compared with a calibration table stored within the EPROM 274 to develop a digital word which is directly proportional to the PPM level of the read ionization current from the sensor 40. The developed digital word is applied to the digital-to-analog converter 276 of FIG. 4B, which in turn applies an analog signal to display the concentration level of the sensed gas on the display 67. The high voltage period counter is decremented until the high voltage period is timed out to complete the warm-up mode.

After the sensor 40 has been warmed up, the main program operates the sensor control system 54 in it's monitoring mode and begins to measure the ionization current drawn from the collector/cathode element 226 of the sensor 40. In particular, the sensed analog ionization current is converted by the analog-to-digital converter 238 to a corresponding digital word. Thereafter that digital word is applied to a calibration look up table, whereby a corresponding digital word indicative of the linear value of the concentration level of the sensed gas is outputted. Thereafter the linearized digital word is converted by the digital-to-analog converter 276 to a corresponding analog signal to be displayed upon display 67. Next, the same digital word indicative of the measured, linearized value of the ion current, is compared with that threshold level entered via the trip point switch 286. If the measured ionization current is below the set threshold level, the program remains in the monitoring mode until a concentration of the sensed gas equal to or greater than the threshold level is determined; then the program moves the gas processing circuit 54b to the next mode, i.e., the leak wait mode.

The purpose of the leak wait mode is to prevent false alarms caused by transient conditions. Basically the leak wait mode establishes a first fixed period and, if the sensed concentration level remains above the threshold level after the first fixed period, a second variable period is timed, whose length is inversely dependent upon the sensed concentration level. If the ionization current falls below the threshold level during the second variable period, a third fixed period is timed before the sensor processing circuit 54b returns to the monitoring mode. It is desired to prevent the random introduction of the test gas from actuating the alarm mode. The alarm mode is entered when there is a continuous introduction of the test gas to be detected, as would be indicative of a valid leak of the refrigerant or halogen gas into the refrigerator system 10. An extraneous sample of the released gas will be quickly removed as the sample pump 38 drives the atmosphere and the gas through the sensor 40. The first period is timed to permit the extraneous sample of the gas to be discharged. If the first fixed period were eliminated, the second period may not last long enough to expel the gas when concentration levels of the gas are relatively large and false alarms might result. If during the first period, further readings of the ionization current fall below the threshold level, the program returns to the monitoring mode to continue measuring the gas concentration. If the first period times out, the second period is initiated and if during that period, the measured gas concentration falls below the set point, the second variable period terminates and a third fixed period is commenced. If the second period times out with the gas concentration level above the threshold level, the program moves to the alarm mode of the gas control system 54. The second period is of a length, which is inversely proportional to its measured concentration of the test gas. In particular, the second period is timed by decrementing a leak wait counter by a value equal to the difference between the measured gas concentration level in PPM and the threshold level. The leak wait counter is decremented at a fixed rate until the second, variable period times out. Thus, the length of the second period is made inversely dependent upon the measured gas concentration level. For maximum detected gas concentration levels, the second period will be relatively short, e.g., two seconds in length. For minimum measured gas concentration levels, the second period may be relatively long, e.g., greater than 3 minutes. If the sensed concentration level falls below the threshold level during the third period, the program returns to the monitoring mode. However, if the sensed concentration level exceeds the threshold level during the third period, the leak wait mode does not restart timing the second variable period but continues directly to time it until completion. In this fashion, the leak wait mode processes sensed concentration levels substantially equal to the set point without unduly delaying the onset of the alarm mode. While the sensor processing circuit 54b is in its leak wait mode, the latch 278 actuates its output driver 280C as to apply a leak wait signal via the conductive path 55 to the system control 56.

After the second period of the leak wait mode has timed out, the sensor control system 54 enters the alarm mode, wherein power is removed from the heater-/anode element 224 and the collector/cathode element 226 of the gas sensor 40. The continued drawing of high levels of ionization current would otherwise shorten the life of the sensor 40. In particular, the life of the sensor 40 is shortened as a function of the amplitude in amps of the drawn ionization current. In other words, when the gas sensor 40 detects relatively high levels of gas concentration, the increased amperage of ionization current significantly decreases the life of the sensor 40 as compared to the detection of relatively low ionization of currents. Thus, it is important to more quickly proceed to the alarm mode when higher levels of gas concentration are detected and thereby to remove power from the sensor 40 and to prolong its life. Also, it is important in the alarm mode to more quickly throw an alarm upon sensing higher levels of gas concentration thus alerting an operator to the presence of the gas in the water output of the condenser 12 shown in FIG. 1. In particular as shown in FIGS. 4A and B, the latch 278 is actuated to remove the HV and filament enable signals from the HV control circuit 268 and the PWM logic circuit 262 respectively, whereby the relatively high voltage and current are removed from elements 224 and 226 of the gas sensor 40. Next, the latch 278 operates the output driver 280d to transmit an alarm message 55 over the path to the system control 56 of FIG. 2A. In addition, the last reading of the gas concentration level is read into a register of the microprocessor 272, whereby that concentration level value may be continuously displayed upon the display 67. Then, the program determines whether a reset signal has been set by the system control 54 before continuing the program. In effect, the program waits until a reset is applied via conduit 63 to the microprocessor 272, at which time the sensor control system 54 is reset to its warm-up mode.

Referring now to FIG. 2A, a further description of the system control 56 will be provided with respect to its structure and method of operation. Illustratively, the system control 56 may take the form of that programmable logical controller as manufactured by Mitsubishi under its Model No. FX-64MT. Such a system control 56 is programmed to control the operations of the fluid sampling and detecting system 20 and, in particular, to repetitively operate the system 20 through a series of liquid test cycles, each cycle comprising the following basic steps: the standby step, the flush step, the fill step, the extraction step, the test step and the drain step. During each of the sequence of liquid test cycles, only one of the plurality of liquid zone valves 76 is energized and thus opened to permit the corresponding one liquid/gas sample to be drawn from that liquid zone coupled to the opened valve 76 to flow into the test chamber 30 and be tested. Between each water test cycle there is a variable delay controlled by a cycle repeat timer, which may be operator set to cause a delay between successive water test cycles of from no delay to almost 100 hours. In addition, the system control 56 performs tests on various of the elements comprising the fluid sampling and detecting system 20 and in particular on its various valves 76, 78, 36 and 50, and the float switches 88 and 90. If any of these parts is detected to have failed, the system control 56 goes to a default or maintenance mode setting its maintenance relay 60, whereby power is removed from the sensor control system 54 and the sample pump 38 and vacuum pump 48.

During each liquid test cycle, the concentration of the test gas within the ambient or background gas (air) about the fluid sampling and detecting system 20 is tested with regard to the threshold level and, if above, the system control 56 sets its maintenance relay 60 to dispose the system 20 into its maintenance mode and its alarm relay 58 to actuate the alarms 104, 106 and 108. When the background gas includes a concentration of the test gas to be detected above the threshold level, that concentration will be drawn into the test chamber 30 and it will be then impossible to distinguish whether the sensor processing circuit 54b is monitoring the test gas released from the liquid/gas sample or from the ambient or background gas. Thus, it is necessary to alert the operator to the presence of a high concentration of the test gas in the background gas.

Each liquid test cycle starts and ends in its standby step. After one cycle has been completed and the system control 56 is in its standby step, the system control 56 deenergizes and thus closes that one liquid zone solenoid valve 76, which was energized in the past cycle, and energizes the next liquid zone solenoid valve 76 in the sequence, thus opening it to permit the flow of the liquid/gas sample from the next zone to the test chamber 30. In this manner, the system control 56 will open and close the liquid zone solenoid valves 76 in sequence, whereby each liquid zone is repetitively sampled one at a time. If a sample from one of the liquid zones has a gas of a concentration above the preset level, the sensor processing circuit 54b is disposed in its alarm mode and an alarm signal is sent to the system control 56, which in turn responds to energize one of the lamps 70a to 70d of FIG. 3B to alert the operator that an alarm condition has occurred in the identified liquid zone and the alarm relay 58 to actuate the alarms.

The system control 56 includes a memory 57, illustratively an EPROM, which stores an alarm flag identifying that water zone in an alarm state so that as the system control 56 continues to test each of the liquid zones in sequence, that liquid zone in the alarm state will be skipped. Even if a high concentration of the test gas is detected in one but not all of the liquid zones, the system control 56 will continue sequencing through and monitoring the remaining liquid zones which are not in an alarm state. If a high concentration of the test gas is detected in all of the liquid zones, the system control 56 sets the maintenance relay 60 disposing the fluid sampling and detecting system 20 into its maintenance mode, whereby power is removed from the sensor control system 54, the vacuum pump 48 and the sample pump 38.

During that portion of each liquid test cycle when the released gas from a liquid/gas sample is not being tested, the system control 56 sequentially actuates each of the gas zone solenoid valves 50b–d associated with the gas manifold 50, whereby gas/gas samples from each of the gas zones are tested. While operating in the drain step, the standby test and a first substep of the flush step, the system control 56 continuously resets a clock after timing a predetermined gas test period, e.g., 60 seconds, before deactuating one of the gas zone solenoid valves 50b–d and then energizing the next gas valve in the sequence. When the liquid test cycle is in the second substep of its flush step, in its test step and in its extract step, the gas test clock of the system control 56 is interrupted. During the second substep of the flush cycle, the system control 56 energizes the gas zone solenoid valve 50a whereby the ambient or background gas is tested immediately before the released gas from the liquid/gas sample is tested. During the remaining portions of the water test cycle, the system control 56 repeatedly opens and closes the gas valves 50b–d at regular intervals, e.g., 60 seconds, to sequentially take the gas/gas samples from the gas zones 2–4. In a further embodiment of this invention, it is contemplated that the concentration level of the test gas in the ambient or background gas is read and that first level is stored in the EPROM 274. Upon subsequently reading a second level of the test gas released from the liquid/gas sample, the stored, first level in the ambient gas is subtracted from the second level and the difference is displayed upon the display 67 of FIG. 3A, whereby the effect of the test gas in the ambient or background gas may be indicated.

The steps of the liquid test cycle will now be described in further detail. Each liquid test cycle starts and ends in the standby step. The system control 56 effects the energization and deenergization of the liquid zone solenoid valves 76 only during a standby step, whereby the liquid/gas sample from the next liquid zone may be tested. At the beginning of the standby step, the system control 56 applies via path 64 signals to deenergize and thus close all of the liquid zones solenoid valves 76a–d and the fill solenoid valve 78 to prevent any liquid/gas sample from the liquid zones to be introduced into the test chamber 30. The drain valve 80 is energized and thus opened, to empty the test chamber 30. The test valve 36 is deenergized, thus closing the test air conduit 34 from the test chamber 30 and opening the test air conduit 34 to the background gas conduit 42, whereby the gas/gas sample from the actuated one of the gas zone solenoid valves 52b–d will be drawn by the vacuum pump 48 to the sensor 40.

The flush step of the liquid test cycle includes two substeps. At the beginning of the first substep, the selected liquid zone solenoid valve 76 and the fill solenoid valve 78 are energized and opened, while the drain valve 80 and the test valve 36 are deenergized and thus closed to permit a sample of the liquid/gas mixture from the selected liquid zone to be conveyed from that liquid zone via the fill conduit 28 and introduced into the test chamber 30. The first substep continues until the liquid level within the test chamber 30 rises to that full level established by the full level float switch 88. At that time, both the full level float switch 88 and the test level float switch 90 are closed and corresponding signals transmitted to the system control 56, which then begins the second substep to deenergize and thus close the selected liquid zone solenoid valve 76 and the fill solenoid valve 78 and to energize and thus open the drain solenoid valve 80, thereby permitting the flush sample in the test chamber 30 to drain therefrom. As the flush sample drains from the test chamber 30, the liquid level lowers thus opening first the full level float switch 88 and then the test level float switch 90. When both the switches 88 and 90 are opened, the system control 56 starts a timer to set a time period, e.g., 90 seconds, in which the test chamber 30 should complete the draining of the sample therefrom. When the 90 second timer times out, the liquid test cycle moves to the next fill step.

The system control 56 also monitors for "flush errors" which may occur during the flush step. The system control 56 initiates a flush error timer to time a period, e.g., 5 minutes in which the complete flush step should be completed. Failure to complete the flush step within the period may occur due to malfunction of any of these liquid zone solenoid valves 76, the fill solenoid valve 78, the drain solenoid valve 80 and the full and test level floats switches 88 and 90. Further, there may be insufficient flow of the liquid/gas sample due to misadjustment of one of the flow control valves 72, insufficient pressure at the liquid zone port 24 because of actions taken up stream, e.g., the refrigeration system 10 associated with that liquid zone has been shut down. If the flush step is not completed within the 5 minute period and the flush error timer does time out, there is an indication of a flush error and the system control 56 actuates its maintenance relay 60 disposing the fluid sampling and detecting system 20 into its maintenance mode.

The flush step introduces a quantity of the liquid/gas sample from the gas zone to be tested through the fill conduit 28 and the test chamber 30 to flush or cleanse any of the sample that may remain from the previous zone. The quantity of the flush liquid/gas sample is set by the height of the full level float switch 88 within the test chamber 30 so the entire interior surface of the test chamber 30 will be flushed.

After the flush step has been successfully completed the liquid test cycle proceeds to its fill step, wherein a predetermined quantity of the liquid/gas sample from the selected liquid zone, is introduced into the test chamber 30. When the fill step is initiated, the selected liquid zone solenoid valve 76 and the fill solenoid valve 78 are energized and thus opened to permit the flow of the liquid/gas sample from the selected liquid zone through the fill conduit 28 and into the test chamber 30, the drain solenoid valve 80 is deenergized and thus closed to permit the test chamber 30 to be filled with the sample of the selected liquid/gas sample and the test solenoid valve 36 is deenergized to close off the test chamber 30 from the test conduit 34 and the sensor 40. The fill step continues as the test chamber 30 is filled with the selected liquid/gas sample until its level rises to close the test level float switch 90. The height of the test level float switch 90 within the test chamber 30 defines the quantity of the liquid/gas sample, e.g., 1 gallon. As illustrated in FIG. 2B, the quantity of the test sample is less than the quantity of the liquid/gas sample introduced into the test chamber 30 during the flush step; the sample of the liquid and the test gas only partially fills the test chamber 30, leaving empty an unfilled volume above the surface of the liquid/gas sample into which the test gas may be released.

During the fill step, the system control 56 tests for two types of fill errors. When the fill cycle is initiated, the system control 56 starts a fill error timer to time a period, e.g., 90 seconds, within which the liquid/gas sample should fill the test chamber 30 to the level of the test level float switch 90. If the test level float switch 90 does not close within that period, a fill error is detected. Additionally, if the full level float switch 88 closes any time during a fill step, a fill error also occurs. When a fill error is detected, the system control 56 switches to its maintenance mode setting both the alarm relay 58 to actuate at least one of the horn 104, the strobe 106 or the combination horn/strobe 108 and, also, to actuate the maintenance relay to remove power. Also, the fill status light 68i is flashed to warn of the fill error. Fill errors may occur due to a faulty liquid zone solenoid valve 76 or fill valve 78, or to failure of the test level float switch 90. Fill errors may also result from low pressure of the liquid/gas sample at the port 24, as described above.

After the fill step has been completed successfully and a known quantity of the selected liquid/gas sample is introduced into the test chamber 30, the system control 56 operates the fluid sampling and detecting system 20 in the extract step. The system control 56 initiates a timer to time a fixed period e.g., 3 minutes, during which the extract motor 86 is energized and each of the fill solenoid valve 78, the selected liquid zone solenoid valve 76, the drain solenoid valve 80 and the test solenoid valve 36 are deenergized and thus closed, whereby the test chamber 30 is sealed. As best shown in FIG. 2B, the known quantity of the liquid/gas sample to be tested, is agitated as the extract motor 86 rotates the propeller 84, whereby trapped bubbles of the gas within the sample are released into that volume of the test chamber 30 above the liquid level.

After completing the extract step, the system control 56 effects the test step, wherein the released gas from the liquid/gas sample within the test chamber 30 is removed from the test chamber 30 and drawn by the sample pump 38 to the sensor 40. As explained above, the sensor 40 is disposed to its monitoring mode to detect concentrations of a particular gas above the threshold level and, if the concentration remains steady above the threshold level for the duration of the leak wait period, the sensor processing circuit 54b provides an alarm signal via the conductor path 55 to the system control 56. At the beginning of the test step, the system control 56 deenergizes and thus closes the selected liquid zone solenoid valve 76, the fill solenoid valve 78 and the drain solenoid valve 80, while energizing and thus opening the test solenoid valve 36 so that the released gas may escape the test chamber 30 only through the test valve 36.

The system control 56 also includes a test timer for controlling the fixed length duration of the test step, during which the sample pump 38 is energized to draw the released gas through the test conduit 34 to the sensor 40. If the test timer times out the fixed period without the sensor 40 detecting the presence of a concentration of the gas above the threshold level, the test step will terminate and the system control 56 will move to the next, drain step.

However, if the sensor 40 and its sensor processing circuit 54b senses a test gas of a concentration above the threshold level, the circuit 54b will enter its leak wait mode and will send a leak wait signal to the system control 56 indicating that the system 54b is in its leak wait mode. The system control 56 responds to such a leak wait signal to interrupt the timing of the test timer until the leak wait signal is removed and the test timer is then reinitiated. In that situation where the gas released into the test chamber 30 is of a level approximately equal to that of the threshold level, the sensor processing circuit 54b may transfer back and forth between its leak wait mode and its monitoring mode. Each time the circuit 54b returns to its leak wait mode, it will transmit to the control system 56 another leak wait signal. When the system control 56 has received three consecutive leak wait signals, the system control 56 will treat the condition of the sensor 40 as an alarm condition and will reset the reset relay 62 to cause the sensor processing circuit 54b to return to its warm-up mode and to move the system control 56 to its next drain step. The system control 56 will also set its alarm relay 58 to provide an alarm to the operator. Thus the test step will be interrupted by the circuit 54b and the system control 50 will remain in its test step until it has received three leak wait signals or an alarm signal from the circuit 54b.

If the sensor processing circuit 54b completes its leak wait mode and moves into an alarm mode, as described above, the sensor processing circuit 54b removes power from the sensor 40 and sends an alarm signal via the conductor path 55 to the system control 56, which responds thereto by setting the alarm relay 58 and the reset relay 62. Upon setting, the reset relay 62 closes a pair of contacts to apply a reset signal via conductor path 63 to the sensor processing circuit 54b, disposing it to its warm-up mode. The system control 56 further responds to the alarm signal from the sensor processing circuit 54b by moving to the next, drain step. Upon receipt of the alarm signal from the sensor processing circuit 54b, the system control 56 sets a timer to time out a fixed period, e.g., 3 minutes, to permit the circuit 54b to complete its warm-up mode to initialize the sensor 40, before the next liquid test cycle is begun.

Upon entering the drain step, the system control 56 deenergizes and thus closes the selected zone solenoid valve 76, the fill solenoid valve 78 and the test solenoid valve 36, and energizes and thus opens the drain solenoid valve 80 whereby the test chamber 30 is otherwise sealed except for the opened drain solenoid valve 80 to permit the escape of the liquid/gas sample therefrom. As the liquid level of the draining liquid/gas sample falls, the test level float switch 90 closes thus initiating a drain timer to time a fixed period, e.g., 90 seconds, to provide adequate time for the liquid/gas sample to drain from the test chamber 30. When the drain timer times out the system control 56 moves to the standby step.

When the drain step starts, a drain error timer is initiated to time a fixed period, e.g., 2 minutes. The drain error timer is reset when the liquid level of the liquid/gas sample within the test chamber 30 falls below the level of the test level float switch 90 and that switch 90 opens. If the drain error timer times out there is an indication that the drain solenoid valve 80 has failed and, as described above, the control system 56 enters its maintenance mode by setting the maintenance relay 60 to remove power from various parts of the system and to actuate the alarm relay 56 to provide a warning to the operator.

As described above, the system control 56 is operative in either a manual or automatic mode. In the manual mode, the system control 56 remains in the selected step until another step is manually selected by actuating the advance switch 68f. The logic within the system control 56 that detects flush and fill errors is active in both the manual and automatic modes. Therefore, if the system control 56 is disposed in its manual mode and it is advanced to either its flush or fill steps, the system control 56 will eventually go into an error condition and the system control 56 will enter its maintenance mode and the maintenance relay 60 set. To reset any of the flush and fill errors, it is necessary to dispose the system control 56 to its manual mode and then advance it to its standby step before actuating the reset switch 68d. When so reset, the system control 56 will dispose the sensor processing circuit 54b to its warm-up mode and the system control 56 is then ready to commence the next liquid test cycle.

In considering this invention, it should be remembered that the present disclosure is illustratively only and the scope of the invention should be determined by the appended claims.

I claim:

1. A method of monitoring a liquid containing a test gas at each of a plurality of zones and of determining the concentration of the test gas within the liquid above a threshold level, said method comprising a repetitively taking Of one sample of the liquid at a time at each of the plurality of zones; for each sample, said sample taking comprising the steps of:
   a) conveying the one sample of the liquid from the one zone to a test chamber;
   b) separating the test gas from the one sample of the liquid conveyed to the test chamber;
   c) conveying the test gas released into the test chamber from the one sample of the liquid taken from the test chamber to a sensor;
   d) operating the sensor to detect the presence of the released test gas of a concentration above the threshold level to produce an alarm indicative thereof;
   e) discharging the one sample taken from the one zone from the test chamber; and
   f) flushing the one sample taken from the one zone from the test chamber with the liquid taken from another zone of the plurality of zones before introducing the next sample of liquid from the other zone into the test chamber.

2. The monitoring method of claim 1, wherein a sampling sequence comprises the steps of taking a series of samples, one from each zone of the plurality of zones in a given order.

3. The monitoring method of claim 2, wherein the sampling sequence is repetitively operated to continuously monitor the gas and liquid in each of the plurality of zones.

4. The method of monitoring of claim 3, wherein there is further included the step of responding to an alarm to identify a corresponding one zone of the plurality of zones from which the sample was taken with a concentration of the test gas above the threshold level, and of deleting the sampling of that identified zone from the subsequent sampling sequences.

5. The method of monitoring of claim 1, wherein for each sample, said sample taking further comprises the steps of taking one sample of the ambient atmosphere and of conveying that sample to the sensor, and of operating the sensor to detect the presence of the test gas in the ambient atmosphere of a concentration above the threshold level to produce an alarm indicating that the detecting of the released gas from a sample of the liquid may be contaminated.

6. The method of monitoring of claim 1, wherein the series of steps following the taking of each sample is repeated to produce a repetitive cycle of steps.

7. The method of monitoring of claim 6, wherein each of said repetitive cycles comprises a further step of taking and conveying a sample of the ambient atmosphere to the sensor before carrying out step c).

8. The method of monitoring of claim 7, further comprising the steps of operating the sensor to take a first reading of the concentration of the test gas in the ambient atmosphere and to take a second reading of the concentration of the test gas in the liquid, and taking and displaying the difference between the first and second readings.

9. The method of monitoring as claimed in claim 7, wherein the step of taking the sample of the ambient atmosphere is carried out during step f) prior to the taking of the next sample of the liquid.

10. The method of monitoring of claim 7, wherein a period between consecutive sampling cycles is varied.

11. A method of monitoring for the presence of a test gas in both of a liquid and of an ambient atmosphere of a concentration above a threshold level, said method comprising a repetitively taking and introducing a series of first samples of the liquid into a test chamber; for each first sample, said sample taking comprising the steps of:
   a) separating the test gas from the liquid of each first sample of the series introduced into the test chamber;
   b) conveying the separated test gas of each first sample to a gas sensor;
   c) repetitively operating the gas sensor to detect whether the concentration of each separated test gas of each first sample is above the threshold level and, if so, to provide an alarm; and
   d) taking and conveying a second sample of the ambient atmosphere to the gas sensor, before operating the sensor to detect whether the concentration of the test gas in the second sample in the ambient atmosphere is above the threshold level and, if so, to provide an alarm indicating that the test gas in the atmosphere may be contaminating a detection by the sensor of the presence of the test gas in the next first sample.

12. Apparatus for taking first samples of a liquid containing a test gas from a plurality of corresponding first spaces and taking second samples of a mixture of the test gas and another gas from a plurality of corresponding second spaces, and for monitoring each of the first and second samples for the presence of the test gas of a concentration above a threshold level, said apparatus comprising:
   a) a plurality of first actuable valves, each of said first actuable valves being connected to a corresponding one of the plurality of first spaces;
   b) a plurality of second actuable valves, each of said second actuable valves being connected to a corresponding one of the plurality of second spaces;
   c) a test chamber connected with each of said first actuable valves for receiving one first sample at a time from an actuated one of said plurality of first actuable valves;
   d) means for separating the test gas from the liquid of the one first sample in said test chamber;
   e) gas detecting means in communication with said test chamber for receiving the separated test gas from the one first sample and with each of said second actuable valves for receiving one second sample at a time from an actuated one of said plurality of second actuable valves; and
   f) controlling means connected with each of said pluralities of said first actuable valves and of said second actuable valves for selectively actuating only one of said first and second actuable valves at a time to permit the detection by said gas detecting means of the test gas in only one the first or second samples at a time.

13. The sample taking apparatus of claim 12, wherein said controlling means repetitively carries out a test cycle for each first actuable valve of said plurality, comprising means operative during each test cycle for successively opening one first actuable valve of said plurality, means for thereafter operating said separating means to separate the test gas from the liquid of the first sample in said test chamber and means for thereafter operating said gas detecting means to detect the test gas from the one first sample.

14. The sample taking apparatus of claim 13, wherein said controlling means further comprises second means for opening only one second valve of said plurality for a fixed time, before closing said one second actuable valve and opening the next second actuable valve of said plurality.

15. The sample taking apparatus of claim 14, wherein said first means defeats said second means from opening said second valves at least during the operation of said gas detecting means in the test cycle to sense the separated gas from the one first sample.

16. Apparatus for monitoring a series of samples of a liquid containing a test gas for the presence of the test gas of a concentration above a threshold level, said apparatus comprising:
 a) means for defining a test chamber;
 b) means for repetitively taking and introducing the series of samples into said test chamber, each sample of said series being of a predetermined quantity;
 c) means for agitating each sample of said series within said test chamber to release the test gas from that sample;
 d) sensor means for detecting the presence of the test gas of the concentration above the threshold level to provide an alarm indicative thereof;
 e) means for repetitively conveying the released gas of each sample of said series from said test chamber to said sensor means; and
 f) means coupled to said agitating means and, upon the introduction of each sample of the series into said test chamber, for operating said agitating means to provide each sample with a predetermined quantity of agitation.

17. The monitoring apparatus of claim 15, wherein said agitating means comprises propeller means positioned to engage each sample of said series within said test chamber and motor means coupled to rotatively drive said propeller means.

18. The monitoring apparatus of claim 17, wherein said control means upon the introduction of one sample of said series into said test chamber actuates said motor means for a fixed period of time.

19. Apparatus for monitoring a series of samples of a liquid containing a test gas for the presence of the test gas of a concentration above a threshold level, said apparatus comprising:
 a) means for defining a test chamber;
 b) means for repetitively taking and introducing the series of samples into said test chamber, each sample of said series being of a predetermined quantity;
 c) means for agitating each sample of said series within said test chamber to release the test gas from that sample;
 d) sensor means for detecting the presence of the test gas of the concentration above the threshold level to provide an alarm indicative thereof;
 e) means for repetitively conveying the released gas of each sample of said series from said test chamber to said sensor means; and
 f) control means responsive to the operation of said agitating means for defeating the operation of said sample taking means and said gas conveying means, whereby said test chamber is sealed to prevent the escape of any released test gas from said test chamber while said agitating means is operative.

20. Apparatus for monitoring a series of samples of a liquid containing a test gas for the presence of the test gas of a concentration above a threshold level, said apparatus comprising:
 a) means for defining a test chamber;
 b) means for repetitively taking and introducing the series of samples into said test chamber, each sample of said series being of a predetermined quantity, said introducing means comprising flow control means for regulating the introduction of each sample into said test chamber at the same flow rate;
 c) means for agitating each sample of said series within said test chamber to release the test gas from that sample;
 d) sensor means for detecting the presence of the test gas of the concentration above the threshold level to provide an alarm indicative thereof; and
 e) means for repetitively conveying the released gas of each sample of said series from said test chamber to said sensor means.

21. Apparatus for monitoring a series of samples of a liquid containing a test gas for the presence of the test gas of a concentration above a threshold level, said apparatus comprising:
 a) means for defining a test chamber;
 b) means for repetitively taking and introducing the series of samples into said test chamber, each sample of said series being of a predetermined quantity;
 c) means for agitating each sample of said series within said test chamber to release the test gas from that sample;
 d) sensor means for detecting the presence of the test gas of the concentration above the threshold level to provide an alarm indicative thereof; and
 e) means for repetitively conveying the released gas of each sample of said series from said test chamber to said sensor means, said conveying means comprising flow control means for regulating the conveying of the released gas from each sample to said sensor means to be of substantially the same flow rate.

22. A method of monitoring a series of samples of a liquid containing a test gas for determining the presence of the test gas within one sample above a threshold concentration, said method comprising the repetitively sampling of the liquid to produce a series of samples, each sample being of a predetermined quantity; for each sample, said sample taking comprising the steps of:
 a) introducing one sample of said series into a test chamber;
 b) imparting a constant amount of agitation to the one sample of said series within said test chamber to release the test gas from the one sample;
 c) conveying the gas released into the test chamber from the one sample of said series to a sensor; and
 d) operating the sensor to detect the presence of the released test gas above the threshold concentration to produce an alarm indicative thereof.

23. A method of monitoring a series of samples of a liquid containing a test gas for determining the presence of the test gas within one sample above a threshold concentration, said method comprising the repetitively sampling of the liquid to produce a series of samples, each sample being of a predetermined quantity; for each sample, said sample taking comprising the steps of:
 a) introducing one sample of said series into a test chamber;

b) agitating one sample of said series within said test chamber to release the test gas from that one sample, while sealing the test chamber to prevent the escape of the released test gas from the one sample;

c) conveying the gas released into the test chamber from the one sample of said series to a sensor; and d) operating the sensor to detect the presence of the released test gas above the threshold concentration to produce an alarm indicative thereof.

24. A method of monitoring a series of samples of a liquid containing a test gas for determining the presence of the test gas within one sample above a threshold concentration, said method comprising the repetitively sampling of the liquid to produce a series of samples, each sample being of a predetermined quantity; for each sample, said sample taking comprising the steps of:

a) conveying at a flow rate one sample of said series into a test chamber and maintaining constant the flow rate of each sample of the series;

b) agitating the one sample of said series within said test chamber to release the test gas from the one sample;

c) conveying the gas released into the test chamber from the one sample of said series to a sensor; and d) operating the sensor to detect the presence of the released test gas above the threshold concentration to produce an alarm indicative thereof.

25. A method of monitoring a series of samples of a liquid containing a test gas for determining the presence of the test gas within one sample above a threshold concentration, said method comprising the repetitively sampling of the liquid to produce a series of samples, each sample being of a predetermined quantity; for each sample, said sample taking comprising the steps of:

a) introducing one sample of said series into a test chamber;

b) agitating one sample of said series within said test chamber to release the test gas from that one sample;

c) conveying the gas released at a flow rate into the test chamber from the one sample of said series to a sensor, and maintaining constant said flow rate; and d) operating the sensor to detect the presence of the released test gas above the threshold concentration to produce an alarm indicative thereof.

* * * * *